United States Patent [19]
Steinhaus et al.

[11] Patent Number: 5,273,049
[45] Date of Patent: Dec. 28, 1993

[54] DETECTION OF CARDIAC ARRHYTHMIAS USING TEMPLATE MATCHING BY SIGNATURE ANALYSIS

[75] Inventors: Bruce M. Steinhaus, Parker; Saul E. Greenhut, Aurora, both of Colo.

[73] Assignee: Telectronics Pacing Systems, Inc., Englewood, Colo.

[21] Appl. No.: 865,320

[22] Filed: Apr. 9, 1992

[51] Int. Cl.⁵ ............................................. A61B 5/0472
[52] U.S. Cl. ..................................... 128/696; 128/702
[58] Field of Search ...................... 128/696, 702, 705

[56] References Cited

U.S. PATENT DOCUMENTS

| | | | |
|---|---|---|---|
| 4,202,340 | 5/1980 | Langer et al. | 128/419 D |
| 4,406,287 | 9/1983 | Nappholz et al. | 128/419 PG |
| 4,408,606 | 10/1983 | Spurrell et al. | 128/419 PG |
| 4,665,485 | 5/1987 | Lundy et al. | 128/702 |
| 4,692,719 | 9/1987 | Whigham | 332/11 D |
| 4,779,617 | 10/1988 | Whigham | 128/419 P |
| 4,821,724 | 4/1989 | Whigham | 128/419 P |
| 5,000,189 | 3/1991 | Throne et al. | 128/702 |

OTHER PUBLICATIONS

D. Lin et al., "Identification of Ventricular Tachycardia Using Intracavitary Ventricular Electrograms: Analysis of Time and Frequency Domain Patterns", PACE, vol. 11, pp. 1592-1605, Nov. 1988, Part I.

Primary Examiner—William E. Kamm
Assistant Examiner—Scott M. Getzow
Attorney, Agent, or Firm—Gottlieb, Rackman & Reisman

[57] ABSTRACT

A method and apparatus for detecting cardiac arrhythmias are disclosed. The detecting method and apparatus sense cardiac electrical signals when the heart is functioning in a known cardiac state, such as a physiologically normal cardiac state, then define and store an array of amplitude windows wherein each sample in the array of amplitude windows corresponds to a sample of the known cardiac signal. Each amplitude window delineates a range of signal amplitudes bracketing the amplitude of the known cardiac electrical signal sample. The array of amplitude windows corresponds in time to periodically occurring known cardiac signal samples occurring within a predetermined time of interest. Subsequently, when the heart is functioning in an unknown cardiac state, the method and apparatus monitor cardiac electrical signals by time aligning samples and comparing, on a sample by sample basis, the amplitude of unknown state cardiac signal samples with the amplitude range within the stored array of amplitude window samples. The relative number of samples falling outside the amplitude windows is the basis for analyzing cardiac signal morphology for the purpose of detecting cardiac arrhythmias.

30 Claims, 7 Drawing Sheets

DETECTION OF CARDIAC ARRHYTHMIAS USING TEMPLATE MATCHING BY SIGNATURE ANALYSIS

TECHNICAL FIELD

This invention relates generally to cardiac control and monitoring devices, including implantable pacemakers, arrhythmia control systems and defibrillators, and more particularly to systems within such devices which, to detect cardiac arrhythmias, perform signal processing and analysis in a manner which accounts for the normal variability of physiological signals and reduces the number of individual computations required and thereby reduces energy requirements.

BACKGROUND OF THE INVENTION

An implantable medical apparatus which executes cardiovascular control operations may evaluate cardiac electrical signals for many purposes. A cardiac control instrument analyzes cardiac signals to determine how well the cardiovascular system is performing. As a result of this analysis, the instrument responds to the detection of predetermined criteria by automatically initiating control operations. One class of signal analyzers examines the time sequence of cardiac signal amplitudes to detect changes in the morphology, or shape, of the cardiac waveform which are indicative of cardiac function.

Most common cardiac control devices, including cardiac pacemakers, employ a rudimentary form of signal morphology analysis. These devices sense the amplitude of intracardiac electrogram signals and compare the instantaneous sensed amplitude to a preset threshold value. If the signal amplitude is larger than the threshold, the pacemaker inhibits its pacing stimulus generation response. Noise, including cardiac signals arising from sources other than those intended for measurement, adversely influences this simple control mechanism.

More sophisticated morphology analysis techniques are required for controlling other, more complex, diagnostic and therapeutic operations. One example of a function requiring a sophisticated analysis technique is the reliable detection of cardiac arrhythmias. The difficult problem of cardiac arrhythmia detection, including detection of ventricular tachycardia and fibrillation, has been addressed using many cardiac signal morphology procedures. One effective procedure, as proven in tests involving both intracardiac signal and surface electrocardiograms and reported by D. Lin et al. in "Identification of Ventricular Tachycardia Using Intracavitary Ventricular Electrograms: Analysis of Time and Frequency Domain Patterns", PACE, Vol. 11, pages 1,592-1,606 (1988), is the correlation of the detected signal with a previously recorded signal waveform which is known to characterize a particular diagnostic condition. Correlation is the summation of the products of point-by-point multiplications of two waveform sequences for the purpose of deriving a standard of similarity between the two waveform sequences. Unfortunately, correlation analysis requires such computational complexity that it is impractical in an implanted device. Because the device expends energy on each computational step and correlation requires so many computations, the lifetime of an implanted device performing correlation would be unreasonably short or the battery size too large for practical usage.

In many cardiac arrhythmia patients, there is a critical need for a reliable method for differentiating sinus tachycardia and atrial tachyarrhythmias from ventricular tachycardia (VT). If a cardiac control device had the capability of distinguishing sinus tachycardia from VT, it could monitor heart activity to determine whether there was a need to perform a procedure for terminating heart disorders or arrhythmias. (This procedure is called cardioversion). Most early methods for differentiating sinus tachycardia from VT were based on analyzing the timing between consecutive R-waves within a sensed electrocardiogram. Diagnostic devices would determine the R-wave rate and compare it to a predetermined maximum rate of sinus tachycardia. Some devices would also analyze the rate stability of the heart and the quickness of the onset of rate changes. Because these rate change characteristics of the R-wave always accompany ventricular tachycardias, a device controlled by these procedures will consistently detect and respond to such arrhythmias. Unfortunately, a normally functioning heart also may exhibit these rate change characteristics. For example, such rate changes may indicate only that the patient is exercising. The morphology of the intracardiac electrogram usually displays morphological differences depending upon whether the heartbeat proceeds in a normal sinus rhythm (SR) sequence of electrical activation or an abnormal ventricular tachycardia (VT) sequence. Therefore, in addition to monitoring the rate, it is beneficial for a device to analyze the morphology of cardiac signals.

Langer et al., in U.S. Pat. No. 4,202,340, entitled "Method and Apparatus for Monitoring Heart Activity, Detecting Abnormalities, and Cardioverting a Malfunctioning Heart", issued May 13, 1980, describe an antitachycardia pacing system which detects arrhythmias by analyzing the morphology of cardiac signals. The arrhythmia detection system of the Langer et al. invention analyzes cardiac signal morphology statistically by developing a probability density function, which compares the amplitudes and locations of points in an analyzed cardiac waveform with the expected locations of points of a predetermined "normal" waveform. When the waveform becomes irregular, as measured by the probability density function, this indicates an abnormal cardiac function. The probability density function defines the fraction of time, on the average, that a signal spends between two amplitude limits. The basis for decision in this process is that the amount of time spent at baseline in each cardiac cycle is significantly longer during sinus rhythm than during ventricular tachycardia or ventricular fibrillation. The probability density function is the measure of time the signal spends away from the isoelectric baseline. It is markedly different during ventricular fibrillation than it is during normal sinus rhythm. The probability density function detects ventricular fibrillation (VF) reliably since the signal is seldom near the isoelectric line during VF. However, the probability density function is not nearly as reliable for distinguishing sinus tachycardia from ventricular tachycardia.

The probability density function approach to arrhythmia detection is often unreliable because a ventricular tachycardia signal often appears the same as a sinus tachycardia cardiac signal to a probability density detector. Furthermore, if the predetermined "normal"

waveform is not properly synchronized with the analyzed waveform, the device may incorrectly classify a waveform as an indication of a fibrillation condition upon the occurrence of some forms of high rate, or even low rate, ventricular tachycardia, in addition to true ventricular fibrillation. A particular problem occurs in the presence of ventricular conduction abnormalities. Defibrillation, which is triggered by a high rate tachycardia, is acceptable because high rate tachycardia can be fatal if it occurs at an elevated rate so considerable that not enough blood is pumped to sustain the body. However, generating defibrillation pulses in the event of low rate, non-life threatening tachycardia is inappropriate and possibly harmful.

Correlation analysis of intra-cavitary ventricular electrograms is another technique for analyzing cardiac waveform morphology. Correlation of signals improves specificity of arrhythmia recognition. Correlation waveform analysis is a reliable technique for discriminating ventricular tachycardia from sinus rhythm. It has been used for over two decades in the analysis of surface lead morphology as well as for analyzing esophageal electrograms, intra-ventricular electrograms and intra-atrial electrograms. However, the number of computations correlation requires is too demanding for usage in the low energy environment of an implantable device.

One technique for performing standard correlation, called piecewise correlation analysis, involves multiplying the waveform sequences in a section by section manner. This provides for a reduction in the number of required computations by limiting the correlation procedure to operate only in the vicinity of the R-wave. In one example of piecewise correlation, a signal processing system defines a representative "normal" signal by measuring a ventricular electrogram signal template when the heart is functioning with a normal sinus rhythm. The system specifies this template by "windowing" the waveform with respect to time, detecting the QRS complex of the cardiac signal and storing a predetermined number of samples before and after the QRS complex. For example, a waveform window may include 64 samples, which contain the QRS complex and are acquired at a 1,000 Hz rate. The system averages a number of these waveform windows for a preset number of cardiac cycles with the QRS complex for each cardiac cycle occurring at the same sample location within the window. After sampling and storing the template waveform, the system samples the ventricular electrogram at the same rate and for the same number of samples as was done when acquiring the template samples. The device correlates these samples with the average sinus rhythm template on a beat-by-beat basis.

U.S. Pat. No. 5,000,189, entitled "Method and System for Monitoring Electrocardiographic Signals and Detecting a Pathological Cardiac Arrhythmia such as Ventricular Tachycardia", issued to R. D. Throne et al. on Mar. 19, 1991, describes another method for comparing cardiac signals for the purpose of detecting arrhythmia conditions. The Throne et al. system monitors electrocardiographic signals for the purpose of detecting cardiac arrhythmias by processing and analyzing such signals when the heart is functioning in an unknown state and comparing these processed signals to heart signals obtained when the heart was operating in a known state. This system defines a known signal template by acquiring electrocardiogram signals when the heart is operating in a known state, calculating the first derivative of the signal, determining the location of zero crossings of the first derivative signal and defining time partitions for analyzing subsequent cardiac signals at the time locations of the zero crossings. The template is determined by summing the samples in each partition. The first derivative of subsequent signals, which are acquired when the heart is functioning in an unknown state, is calculated and summed within the partitions defined by the template signal. The partition sums for the subsequent samples and the template samples are compared to determine whether the unknown signals have the same characteristic structure as the known template signals. The method and system of the Throne et al. patent improves upon the standard correlation procedure by requiring much simpler computations and demanding less power for performing calculations. It is an advantage that the Throne et al. system functions independently of fluctuations of the zero level (baseline) between ventricular electrocardiograms and changes in electocardiogram amplitudes.

The previously known morphology-based arrhythmia detection procedures operate on the presumption that the monitored signal must have the same form, in terms of timing and phase, as a template signal which was acquired when the heart was functioning in a known cardiac state. These procedures consider any changes in form to be errors, which are to be tolerated to some degree, but are errors nonetheless. Moreover, previously known morphology-based arrhythmia detection procedures respond to single large amplitude noise spikes by including an aberrant sample amplitude in a calculation for determining a physiological parameter. This single noise sample will often greatly skew the parameter value resulting from the calculation in a manner which is out of perspective to its physiological importance.

It is, therefore, a primary object of the present invention to provide for analysis of cardiac electrical signals in a manner which considers physiological variability in signal morphology to be a normal occurrence, so that normal physiological variations in the signal will not contribute to an increase in an "error" signal in the derived physiological parameter. This is done by selecting a physiologically normal cardiac electrical signal, defining an amplitude window which delineates a range of signal amplitudes bracketing the amplitude of the normal cardiac electrical signal, and comparing subsequent cardiac signals to the normal window in a sample-by-sample manner. The relative number of samples falling outside the amplitude window, rather than the cumulative amplitude of the differences between samples, is used to analyze signal morphology for the purpose of detecting cardiac arrhythmias.

Another important object of the present invention is to reduce the emphasis of single noise spikes to a reasonable physiological importance.

It is a further object of the present invention to provide a system for reliably detecting abnormal ventricular signals, based on the morphology of such signals, in which the system accepts physiological variability as a normal condition and is not overly sensitive to the occurrence of short-term noise spikes.

An additional object of the present invention is to provide a low power demand device and a reliable detection circuit to accurately identify ventricular tachycardia and ventricular fibrillation.

Further objects and advantages of this invention will become apparent as the following description proceeds.

SUMMARY OF THE INVENTION

In accordance with one aspect of the present invention, a method and apparatus for monitoring cardiac electrical signals to detect functional abnormalities, such as cardiac arrhythmias of a patient's heart, are provided in a cardiac control or monitoring system. The monitoring method and apparatus of this invention sense cardiac electrical signals when the heart is functioning in a known cardiac state, such as a physiologically normal cardiac state, then characterize this known cardiac state by defining, for each sample of the cardiac signal occuring within a predetermined time of interest, an amplitude window which delineates a range of signal amplitudes bracketing the amplitude of the known cardiac electrical signal. The amplitude windows for each of the consecutive samples of the cardiac signal falling within the predetermined time of interest are grouped to define a template of time sequence samples. The predetermined time of interest is normally selected, in terms of activation and duration, to encompass the time during which a physiologically meaningful signal, such as an R wave, is occurring. The method and apparatus define and store the template in the form of a time sequence of amplitude window samples which envelop or bracket, in amplitude and time of occurrence, events of interest within the waveform of the cardiac electrical signals sensed when the heart was functioning in a known cardiac state. The method and apparatus allow testing during multiple different cardiac states, in addition to the physiologically normal cardiac state, and provide for storage of template windows associated with each state. Thereafter, when the heart is functioning in an unknown cardiac state, the method and apparatus monitor cardiac electrical signals by aligning the unknown cardiac sequence samples such that the periodic features of the unknown cardiac sequence occur at the same time as the periodic features of the template sequence. The method and apparatus then compare each sample of the unknown cardiac state sequence with its time-associated template window sample in a sample-by-sample manner to determine the relative number of unknown cardiac state samples falling outside the relevant amplitude window in comparison to the number of samples falling within the window. The method and apparatus use this relative proportionality of cardiac signal samples falling within and outside of the amplitude windows to analyze signal morphology for the purpose of detecting cardiac arrhythmias. The method and apparatus classify the functionality of the patient's heart as a known cardiac state when the determined relative proportion meets a predetermined criteria and, otherwise, classify the functioning of the patient's heart as outside the known cardiac state.

The method and apparatus include an amplitude normalization capability which provides for continued reliable functionality and appropriate detection of ventricular arrhythmias even in the presence of signal amplitude variations which may arise from various physiological conditions, such as sinus tachycardia. The method and apparatus normalize the amplitude signal by amplifying all samples when the sum of the absolute values of all samples of the unknown cardiac state signal amplitude is smaller than a preset level. This level is defined as a predetermined percentage of the sum of the absolute values of the template samples. If the sum of the absolute values of all samples of the unknown cardiac state signal amplitude is larger than a predetermined level, a multiplication factor times the sum of the absolute values of the template samples, the method and apparatus attenuate the samples.

In accordance with another aspect of the present invention, the method and apparatus perform alignment of the unknown cardiac sequence samples with respect to the template sequence samples by defining an alignment pointer which equates, in time, a sample in the unknown cardiac state sequence with a sample in the template window sequence. The method and apparatus then derive a parameter based on the sample-by-sample differences between the unknown cardiac state and the template window sequences. One such parameter is the sum over all template samples of the absolute values of the difference between each associated signal and template sample. The method and apparatus shift the alignment pointer to determine the parameter value for numerous positions of the unknown cardiac signal sequence with respect to the template sequence. The method and apparatus repeat the shifting and deriving operations over numerous possible alignment combinations and compare the derived parameters to determine the best match between the unknown cardiac state sequence and the template sequence.

In accordance with another aspect of the present invention, a method and apparatus monitor cardiac electrical signals to detect functional abnormalities by sensing cardiac electrical signals when the heart is functioning in a known cardiac state, such as a physiologically normal cardiac state, and characterizing and storing this known cardiac state as a time sequence of template samples, encompassing the samples occurring during a predetermined time of interest during which a physiologically meaningful signal, such as an R-wave, takes place. The apparatus and method then define an amplitude window for each template sample, which delineates a range of signal amplitudes bracketing the amplitude of the known cardiac electrical signal. The amplitude windows for each of the consecutive samples of the template falling within the predetermined time of interest are stored to define an arrary of amplitude ranges with each range associated with a template sample. In this manner, the apparatus and method store the template samples and the corresponding amplitude range array samples. The amplitude range array designates, for each template sample, the variation in amplitude by which a subsequent cardiac signal sample may differ from the corresponding template sample and still be considered similar to a "known" cardiac signal sample. Thus, the apparatus and method encode and store template window data in a form allowing future reconstruction of the template and its amplitude range window. Later, the method and apparatus monitor a time sequence of cardiac electrical signal samples when the heart is functioning in an unknown cardiac state by reconstructing the template window sequence from the stored template and its amplitude range window data, time aligning samples of the unknown cardiac state sequence with respect to said reconstructed template window sequence and comparing the time-aligned samples of the unknown cardiac state sequence with the reconstructed template window sequence in a sample-by-sample manner. The method and apparatus then determine the relative number of time-aligned samples of the unknown cardiac state signal sequence falling outside of the reconstructed template window sequence in comparison to samples lying within the window. If the number of samples outside the template window is larger than a predetermined threshold value, then the method and apparatus conclude that an unknown cardiac state has occurred for the purpose of detecting cardiac arrhythmias.

BRIEF DESCRIPTION OF THE DRAWINGS

While the specification concludes with claims particularly pointing out and distinctly claiming the subject matter regarded as the invention herein, it is believed that the present invention will be more readily understood from the following description, taken in conjunction with the accompanying drawings, in which:

DETAILED DESCRIPTION

Figure 1:
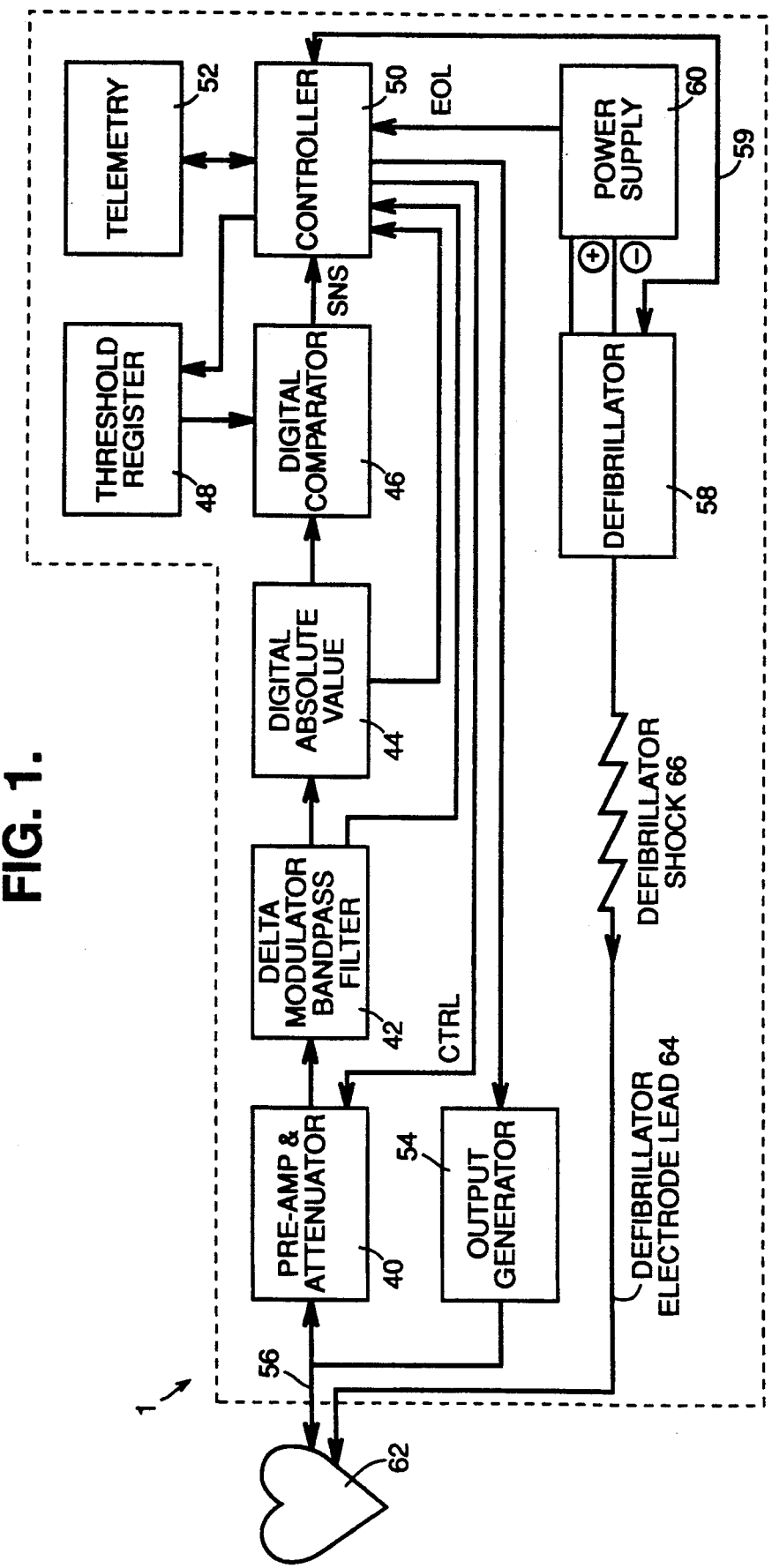
FIG. 1 is a block diagram of a cardiac control device in the form of an implantable antitachycardia pacemaker in which the system of the invention may be incorporated.

Referring to FIG. 1, there is depicted a block diagram of a cardiac control system in the form of an antitachycardia pacemaker 1. Although the preferred embodiment of the invention, an arrhythmia detector, is described as comprising one part of an implantable antitachycardia pacemaker and defibrillator, it is to be understood that the invention is intended for usage, in general, in any cardiac control and monitoring device which senses cardiac electrical signals. Such devices may include bradycardia cardiac pacemakers, electrical sensing drug infusion pumps, and internal and external cardiac monitors and electrophysiology recorders.

Antitachycardia pacemaker 1 is designed to be implantable in a patient and includes an output generator 54, which is controlled by commands from a controller 50, and appropriate leads 56 for electrically connecting the output generator 54 to a patient's heart 62. The leads 56 also connect the patient's heart to sensing circuitry, beginning with a preamplifier and attenuator 40. If the antitachycardia pacemaker 1 is a dual chamber device, leads 56 will generally include an atrial cardiac lead pair extending to the atrium of the patient's heart for sensing of atrial cardiac electrical activity and for the administration of pacing therapy to the atrium, and a ventricular cardiac lead pair extending to the ventricle of the patient's heart for sensing of ventricular cardiac electrical activity and for the administration of a pacing therapy, cardioversion or defibrillation to the ventricle. In a single chamber device, leads will generally include a lead pair to only one of the heart chambers.

Commands from controller 50 to output generator 54 determine which cardiac chamber is stimulated and regulate the timing, amplitude, duration, and stimulus pulse waveform of the delivered pacing therapy. The controller 50 may, in response to inputs received from a digital absolute value block 44 and various inputs received from a digital comparator 46 or a telemetry block 52, perform various operations so as to generate different control and data outputs to both the output generator 54 and a defibrillator 58. A power supply 60 provides a reliable voltage level to the antitachycardia pacemaker 1, including the controller 50 and the defibrillator 58 by suitable electrical conductors (not shown). Defibrillator 58 produces a high voltage to charge its capacitors (not shown) and then discharges them in response to control signals from the controller 50. A defibrillator electrode lead 64 transfers the energy of a defibrillator shock 66 from the implanted antitachycardia pacemaker 1 to the heart 62.

Signals received from the telemetry block 52 permit an external programmer (not shown) to change the operating parameters of antitachycardia pacemaker 1 by supplying appropriate signals. Thus, it is also possible for an external programmer to control operation of defibrillator 58 by means of signals provided to the controller 50.

The controller 50 receives various status and/or control inputs from the digital comparator 46 and the defibrillator 58, such as a sense signal (SNS) from the digital comparator and signals via a bidirectional bus 59 from the defibrillator 58. The controller 50 performs operations, such as arrhythmia detection, and produces outputs, such as pace stimulation control of the output generator 54. In this manner, the controller 50 determines the characteristics of pacing, such as pulse energy and the heart chamber to be stimulated, that is to take place. The controller generates other control outputs to deliver a shock to the patient, to dump the shock to an internal load within the defibrillator 58, to control the charge of a capacitor (not shown) within the defibrillator which determines the voltage level of the shock to be delivered, and to provide a digital signal representative of charge voltage from an analog-to-digital converter (not shown) within defibrillator 58, thus providing a feedback loop which assures that a shock of proper energy level is delivered by defibrillator 58.

The preamplifier and attenuator 40 amplifies the electrical signal from the heart by a gain of 30 in the preferred embodiment of the invention. An eight bit control signal from the controller 50 sets a variable attenuator setting in the attenuator between 0 and 255/256 to attenuate or scale the input signal. A change in the attenuator setting affects the voltage deviation required at the sensing electrode for a sense to be registered. A delta modulator and bandpass filter 42 receives analog signals from preamplifier and attenuator 40, filters the incoming data, and converts it to digital form. A preamplifier and attenuator circuit and a delta modulator and bandpass filter circuit which are suitable for a device which incorporates the arrhythmia detector of the present invention is described in two patents by R. H. Whigham, U.S. Pat. No. 4,692,719, entitled "Combined Pacemaker Delta Modulator and Bandpass Filter" and issued Sep. 8, 1987, and U.S. Pat. No. 4,779,617, entitled "Pacemaker Noise Rejection System" and issued Oct. 25, 1988, and one patent by R. H. Whigham et al., U.S. Pat. No. 4,821,724, entitled "Pacing Pulse Compensation" and issued Apr. 18, 1989.

Figure 2:
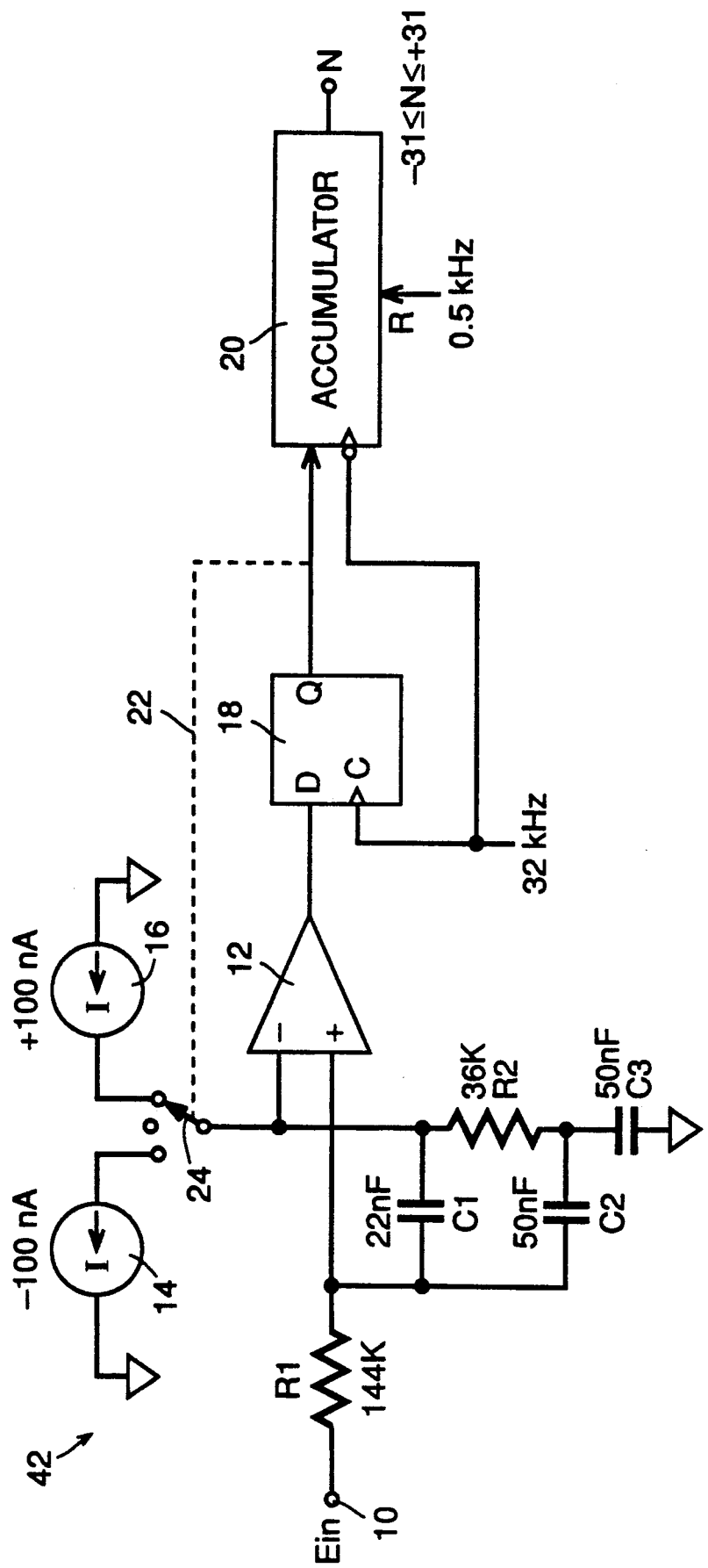
FIG. 2 is a schematic block diagram of a combined delta modulator and bandpass filter circuit which is one of the elements of FIG. 1.

FIG. 2 represents a more detailed diagram of the combined delta modulator and bandpass filter 42 which operates on a pacemaker sense input signal $E_{in}$ from the preamplifier and attenuator 40 of FIG. 1. This circuit performs delta modulation and bandpass filtering using a single amplifier, thereby requiring less power to operate the antitachycardia pacemaker. In FIG. 2, input signal E is applied to terminal 10 through a resistor R1 to the plus input of a differential amplifier 12. The output of the differential amplifier is applied to the D input of a flip-flop 18, which is clocked at a 32 kHz rate. The Q output of the flip-flop 18 reflects the state of the input at the preceding clock pulse. A dashed line 22 represents control over a switch 24, which is shown in the position resulting when the Q output of the flip-flop is high. A +100 nA current source 16 electrically interconnects with the circuit according to the position of the switch 24, as shown. Alternatively, the switch 24 may interconnect a −100 nA current source 14 with the circuit in response to an opposite state of the flip-flop 18. The switch 24 may also take an intermediate position, which interconnects neither current source to the circuit. When current does flow, it flows through three capacitors, one (C1) having a given magnitude and two (C2 and C3) having the same magnitude which may be different from the magnitude of C1. The capacitors C1, C2 and C3 and resistors R1 and R2, in combination with the differential amplifier 12, perform bandpass filtering of the pacemaker sense signal.

By virtue of control line 22, which determines the position of switch 24, the circuit operates as a delta modulator in response to changes in the input signal $E_{in}$. For example, when the input signal $E_{in}$ increases such that the plus input potential to differential amplifier 12 becomes larger while the minus input potential to differential amplifier 12 remains at virtual ground, the amplifier output goes high. The next 32 kHz clock pulse causes the Q output of flip-flop 18 to go high, causing current to flow from the current source 16 through capacitor C1. As a consequence, this restores the potential at the minus input to the differential amplifier 12 to return the potential difference between the minus and plus potential connections to the differential amplifier 12 to the quiescent level. In a similar manner, when the input signal $E_{in}$ decreases to lessen the potential difference between the plus and the minus inputs to the differential amplifier 12 and to bring the amplifier output low, the flip-flop 18 resets. This causes control line 22 to set switch 24 and connect the circuit with current source 14, driving the current through C1 and reducing the potential at the minus input to the differential amplifier 12 to the quiescent level. Accordingly, the output of the differential amplifier 12 serves the dual purposes of controlling the switch to the current sources and representing a bit sample indicative of the manner in which the input signal is changing.

The differential amplifier minus input is a virtual ground. Capacitor C1 is charged and discharged by the current sources so that the potential at the input is increased or decreased by a capacitor potential to create a result in which the potential at the minus input to the amplifier is equal to a reference potential at the plus input. In a quiescent condition, the flip-flop output is alternating 0 and 1 bit samples. A change in the potential at the input causes the flip-flop output to convert to a number of bit samples of the same value until the capacitor charges or discharges to an extent which ...pensates for the change at the input. In this manner, the number of bit samples of constant value at the output of the delta modulator represents the magnitude of the change in the input signal. The value of the output bits depicts the direction of the change.

The output of flip-flop 18, a sequence of bit values expressing changes in the input signal over time, is applied to the data input of an accumulator 20, which is also clocked at the 32 kHz rate (actually 32,768 Hz), but on alternate phases. During each clock cycle, after the flip-flop state is established, the accumulator count increments or decrements according to the state of the flip-flop. The accumulator resets at a 0.5 kHz rate. During each 2 millisecond accumulator cycle, there are 64 clock pulses. The flip-flop is clocked for 62 of these clock pulse cycles to delta modulate the input signal. In the remaining two clock pulse cycles, the flip-flop is not clocked, the switch 24 connects neither current source to the circuit, and the circuit performs "housekeeping" functions such as loading a register from the accumulator, resetting the accumulator, and balancing the current sources. When the accumulator is reset, it takes the value of −31. Therefore, every 2 milliseconds the accumulator provides a sum of the string of 62 zero and one bits to produce an output number N between, and including, the limits of −31 and +31. The controller 50 of FIG. 1 may read this output every other 0.5 kHz cycle to provide a sampling frequency of 500 Hz. In an alternative embodiment of the invention, an additional accumulator (not shown) may sum the values within the 2 millisecond accumulator to provide for a lower sampling frequency. For example, an accumulator may sum two consecutive 2 ms samples to provide 250 Hz samples with values ranging from −62 to +62.

Again referring to FIG. 1, the digital data signal from the delta modulator and bandpass filter circuit 42 progresses both to a digital absolute value circuit 44 and to the controller 50. The digital absolute value circuit derives the absolute value of the digital data signal and delivers it to a digital comparator 46. The digital data signal passes to the controller 50 without absolute value rectification to preserve signal polarity information for further processing.

The controller 50 presets a threshold value into a threshold register 48 which the digital comparator 46 compares with the absolute signal value from block 44. If the absolute signal value is greater than the threshold, the digital comparator generates a sense wakeup signal (SNS) to notify the controller 50 of such an event. Note that in a dual chamber device the signal SNS includes a signal for both the atrium and the ventricle.

The controller 50, which may be a microprocessor, controls all operations of the antitachycardia pacemaker 1. In the preferred embodiment of the invention, the arrhythmia detector is a software routine performed by the controller 50. It is to be understood that the invention is not limited to a software implementation but may also be embodied in other forms including analog and/or digital electronic circuits.

More particularly, the controller 50 writes command signals to the output generator 54 to determine, in a dual chamber device, which heart chamber is stimulated and to set the stimulating pulse timing, amplitude, duration, and morphology of the stimulating pulse. For example, the controller 50 sets the pulse delivery parameters for the purpose of charge balancing a stimulus output. The controller 50 sets the sensing sensitivity and threshold by writing attenuator settings to the preamplifier and attenuator circuit 40, and threshold settings to the threshold register 48, respectively. In a dual chamber device, there are separate attenuator and threshold settings for each heart chamber. The controller receives sensed signals from the delta modulator and bandpass filter 42 and governs the timing and number of intracardiac electrogram samples in addition to determining and executing any signal filtering required for signal analysis. As the controller 50 performs signal sampling, it carries out the analysis necessary for the diagnostic purposes of the pacemaker, as described below.

Telemetry circuit 52 provides a bidirectional link between the controller 50 of antitachycardia pacemaker 1 and an external device such as a programmer. It allows data such as the operating parameters to be read from or altered.

A template matching procedure requires some means for determining when a signal of interest occurs. For template matching procedures which analyze cardiac signals, the signal of interest normally begins with a P-wave, lasts through the duration of a QRS complex and may include a T-wave. The standard timing marker for cardiac signal analysis is the R-wave of the QRS complex, which sets forth the time of ventricular depolarization. To reliably detect R-waves, the controller 50 (FIG. 1) performs an automatic procedure for setting the sensing threshold which the controller writes to the threshold register 48 (FIG. 1). The controller should set the value of the threshold so that false detections of R-waves do not occur but true R-waves are not missed. One procedure for appropriately and automatically setting sensing threshold, which may be employed in the arrhythmia control apparatus of the present invention, is described in conjunction with the flow chart of FIG. 3. Other cardiac signal sensing schemes, which are known in the art of cardiac pacemakers, may be used in place of the following procedure.

Figure 3:
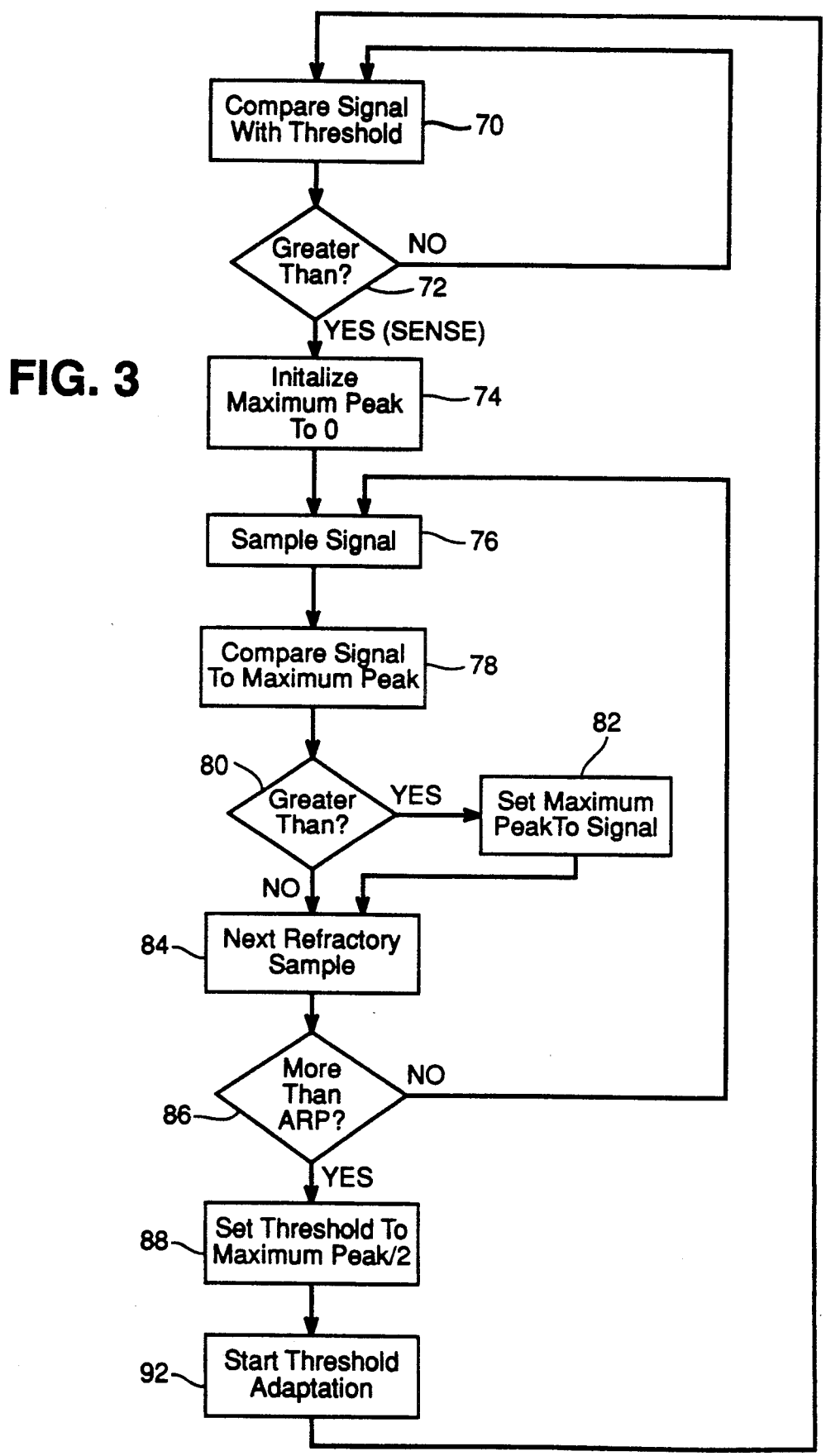
FIG. 3 is a block diagram flow chart of an adaptive linear decaying sensing threshold procedure which is employed in the apparatus of the present invention.

Referring to FIG. 3, there is illustrated a block diagram flow chart of an adaptive linear decaying sensing threshold procedure which may be performed by the controller 50 of FIG. 1. A compare-signal-with-threshold block 70 compares the amplified and delta modulated signal from the digital absolute value block 44 of FIG. 1 with a dynamically-set sensing threshold level. If the signal is greater than the dynamic sensing threshold, then a "SENSE" signal is evoked which indicates the presence of natural cardiac activity. A greater-than logic block 72 controls the branching control operation in response to the comparison of block 70. If the signal is smaller than or equal to the dynamic threshold, under the control of logic block 72, subsequent incoming signals are compared with the dynamic threshold until the threshold value is surpassed. Although a controller may perform this comparison operation and its associated control branching, in the preferred embodiment of the invention, the comparison is performed by a hardware comparator such as the digital comparator 46 of FIG. 1, in which the SNS signal output from the digital comparator is the "SENSE" signal.

While the compare and logic operations of blocks 70 and 72 are taking place, a parallel operation of threshold adaptation is taking place. Discussion of initialization of this operation takes place in conjunction with the description of start-threshold-adaptation block 92 of FIG. 3. The threshold adaptation procedure is delineated in the discussion of FIG. 4.

After a "SENSE" signal occurs, initialize-maximum-peak-to-0 block 74 sets the maximum peak memory location to zero to allow determination of a new maximum peak for the next cardiac cycle. In sample-signal block 76, the controller continues to input regularly timed (for example, 4 ms interval) signals from the delta modulator and bandpass filter block 42 of FIG. 1. Compare-signal-to-maximum-peak block 78 compares each incoming signal to the maximum peak and, under the control of greater-than logic block 80, sets the maximum peak to the incoming signal in set-maximum-peak-to-signal block 82 when it is larger than the previously determined maximum peak. In next-refractory-sample block 84, the controller determines whether the next sample will remain within the absolute refractory period (ARP) interval (for example, 100 ms). Under the control of a more-than-ARP logic block 86, the controller continues to sample refractory sample signals in block 76 if the refractory interval has not ended. After the refractory interval is complete, set-threshold-to-maximum-peak/2 block 88 sets the dynamic threshold to half the maximum peak found during the refractory interval. The controller enables sensing and starts a threshold adaptation procedure in block 92. Control of the procedure returns to the compare-signal-with-threshold block 70 to complete a cardiac cycle.

Figure 4:
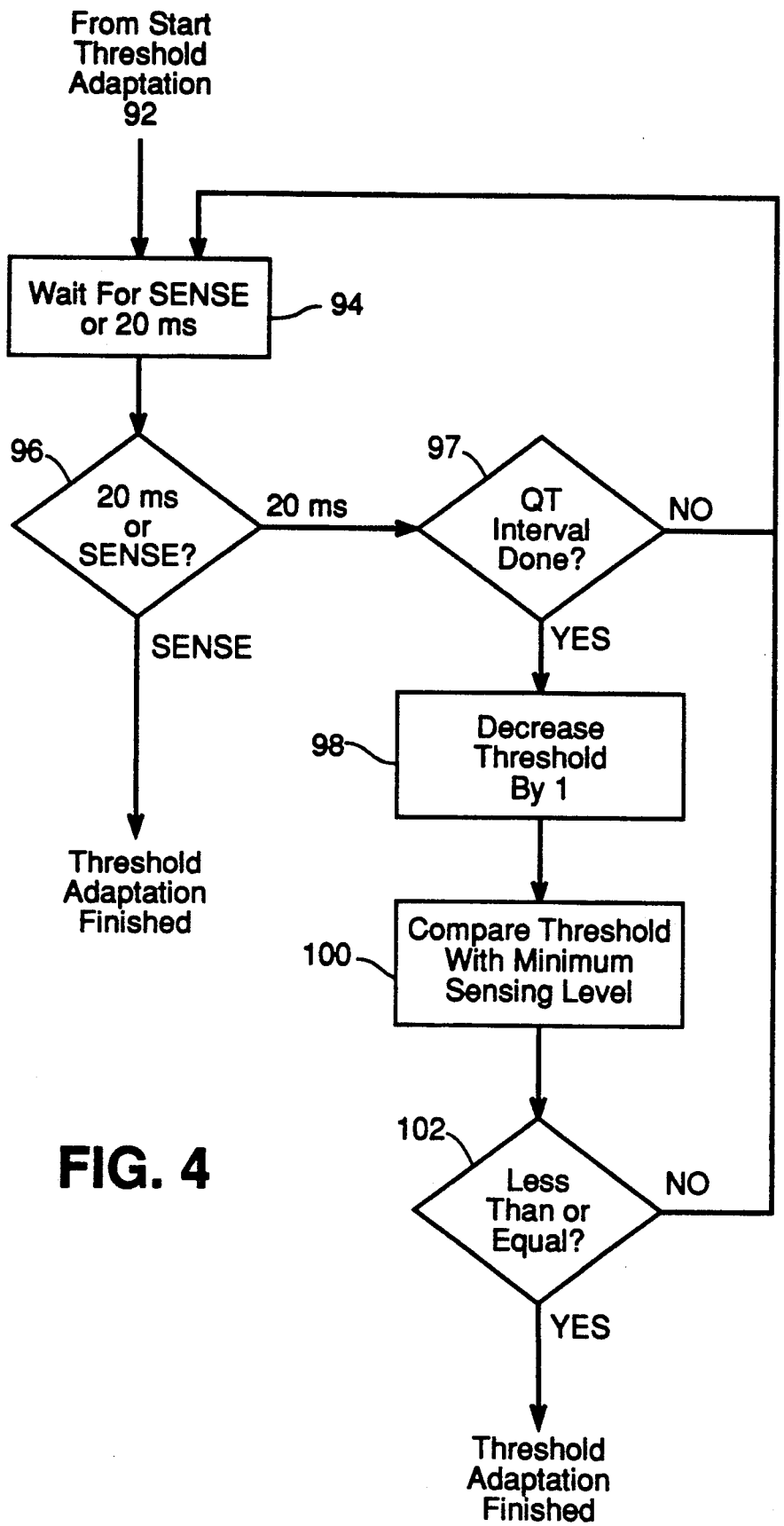
FIG. 4 is a block diagram flow chart which illustrates a threshold adaptation procedure that is one of the elements of FIG. 3.

FIG. 4 is a block diagram flow chart that illustrates this threshold adaptation procedure, which may be performed by the controller 50 of FIG. 1. The threshold adaptation procedure occurs in parallel with blocks 70 and 72 of FIG. 3. In wait-for-SENSE-or-20-ms block 94, the controller waits for the "SENSE" signal, for example arising from the digital comparator 46 of FIG. 1, or for a 20 ms wakeup timer (not shown) within the controller. If a "SENSE" signal occurs, the threshold adaptation procedure is finished due to its termination by the 20-ms-or-SENSE logic block 96. Otherwise, upon a 20 ms wakeup, the controller tests an internal timer (not shown) to determine whether the heart is functioning inside or outside of a QT interval, the time when the heart is finishing its depolarization and repolarization phases. If the time is past the QT interval, QT-interval-done logic block 97 directs the threshold adaptation procedure to decrease the threshold in block 98. Otherwise, QT-interval-done logic block 97 directs the threshold adaptation procedure to return to block 94 to wait for the next sense or timer event.

A physician, using a telemetric programmer (not shown) may set the duration of the QT interval according to the needs of a particular patient. Alternatively, the pacemaker may set the QT interval duration dynamically in response to variations in the patient's heart rate, wherein a higher heart rate should correspond to a shorter QT interval, within bounds set by a physician. In either case, the controller waits for the predetermined QT interval, for example 400 ms, before decreasing the dynamic threshold value by one in block 98 and then comparing the dynamic threshold value with a predetermined minimum sensing level in block 100. If the dynamic threshold, after being decremented, is greater than the minimum sensing level, under control of logic block 102, the controller continues to wait for a "SENSE" signal or the next 20 ms wakeup in block 94. In this manner, the threshold remains constant for the predetermined QT interval after a "SENSE" signal, then it is decremented by one every 20 ms until either a "SENSE" occurs or the minimum sensing level is reached. The minimum sensing level is determined according to an automatic gain level set procedure that is discussed in conjunction with a template acquisition procedure, which is specified hereinafter. If the controller reaches the minimum sensing level, the sensing threshold remains at this value until a "SENSE" signal occurs, at which time the threshold adaptation procedure is repeated.

Figure 5:
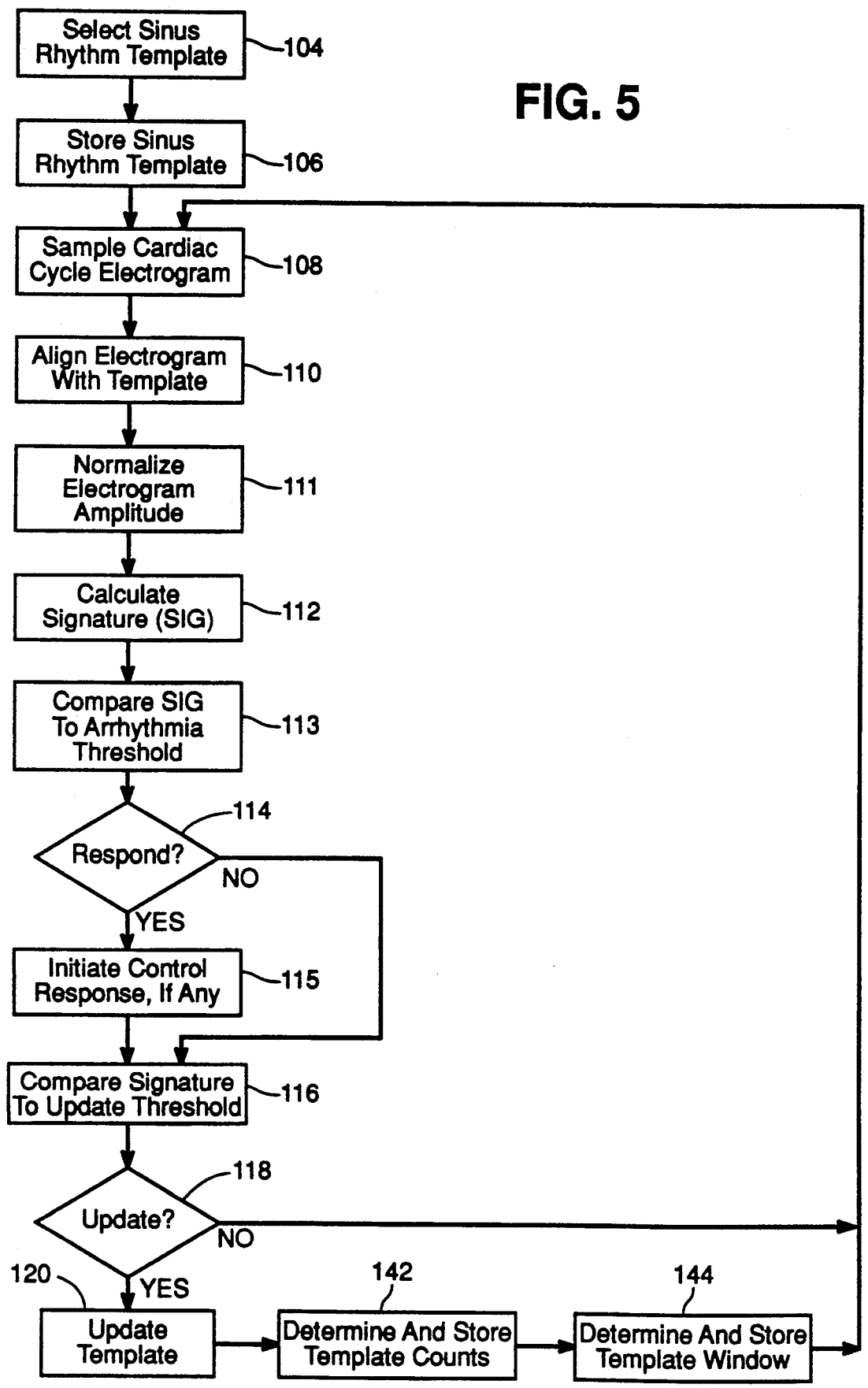
FIG. 5 is a block diagram flow chart of an arrhythmia detection procedure utilized in the present invention.

Referring to FIG. 5, there is shown a block diagram flow chart of an arrhythmia detection procedure which is performed by the controller 50 of FIG. 1 in the preferred embodiment of the invention. A select-sinus-rhythm-template block 104 acquires the template which is the basis for comparison in determining whether sensed signals indicate the presence of a cardiac arrhythmia condition. One such arrhythmia condition is ventricular tachycardia. After selection of the template in block 104, the controller defines a template amplitude "window", which allows for physiological variability of the cardiac signal, and stores the template in memory in store-sinus-rhythm-template block 106. The procedures of blocks 104 and 106 are initialization procedures which are discussed in detail in conjunction with the description of FIG. 7 hereinafter.

After the initialization procedures of blocks 104 and 106, the controller continuously performs the loop of operations in blocks 108 through 120 for subsequent cardiac cycles. Each pass through this loop corresponds to one cardiac cycle. In sample-cardiac-cycle-electrogram block 108, the controller reads a stream or sequence of incoming signal data from the delta modulator and bandpass filter block 42 of FIG. 1. The controller may input and store every sample for the duration of a cardiac cycle or may input only a predetermined number of samples preceding and following either the occurrence of a "SENSE" signal generated by the digital comparator 46 of FIG. 1 or the location of the peak sensed electrogram signal of the cardiac cycle.

After acquiring the electrogram, align-electrogram-with-template block 110 performs data alignment to "synchronize" the waveform of the incoming signal with the template waveform. A "best fit" alignment procedure determines an alignment which matches the signal and template waveforms most closely, using an area of difference (AD) method of comparison, according to equation 1:

$$AD = \sum_{i=1}^{N} |t_i - s_i| \quad (1)$$

where $t_i$ are the template samples, $s_i$ are the signal samples and N is the total number of samples in the template. The minimum AD corresponds to the alignment of samples in which the best fit is obtained between the signal and the template. An AD value of zero corresponds to a perfect match.

Signal alignment may be accomplished using other procedures. For example, the controller may align the sequences so that the maximum amplitude signal sample coincides with the maximum amplitude template sample. Alternatively, the controller may align the sequences according to the timing of the SNS signal generated by the digital comparator 46 of FIG. 1 or may determine the differences between each sample and its sequentially previous sample and align the waveforms according to the maximum difference (having a like sign). In another alternative, the controller may align the waveforms by performing the signature coefficient (SIG) calculation of equation (5), discussed hereinafter, and aligning the waveforms so that the maximum signature coefficient SIG factors coincide. The alignment method of equation (1) was chosen, despite requiring more computations than some other methods, because it produces a superior alignment correspondence.

Next, the controller normalizes the electrogram amplitude in block 111. Physiological signals may vary in amplitude over time. For example, sinus tachycardia or atrial tachyarrhythmias may alter the amplitude of the ventricular signal. Normalize-electrogram-amplitude block 111 compensates for such variations by comparing the sum of the absolute values of the signal samples to the sum of the absolute values of the template samples. The method of normalization is shown below in equations 2, 3 and 4:

$$\text{If } \sum_{i=1}^{N} |s_i| < 0.75 \times \sum_{i=1}^{N} |t_i|, \text{ then } 2s_i \rightarrow s_i, \quad (2)$$

$$\text{If } \sum_{i=1}^{N} |s_i| > 1.5 \times \sum_{i=1}^{N} |t_i|, \text{ then } s_i/2 \rightarrow s_i, \quad (3)$$

$$\text{Otherwise } s_i \rightarrow s_i, \quad (4)$$

where $s_i$ are the signal samples after alignment with the template and $t_i$ are the current template points. This adjustment for electrogram amplitude is intended to maintain the template samples within the signature window for amplitude changes ranging from 0.25 to 3 times the template amplitude range. This level of variation compensates for physiological variability.

Figure 6:
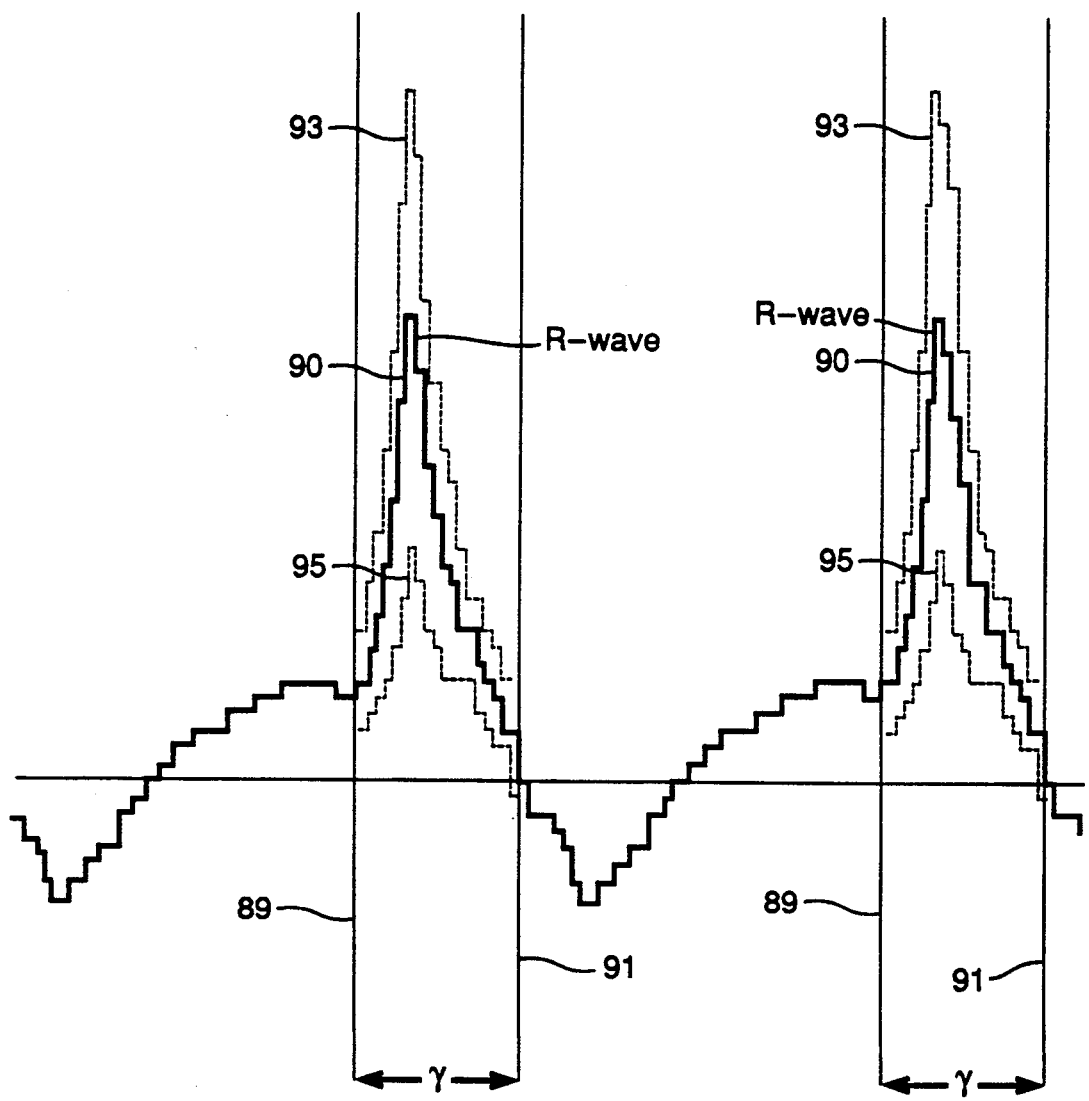
FIG. 6 is an illustration of a sample intracardiac electrogram signal waveform indicating a normal sinus rhythm cardiac behavior, which may be used as a template signal for signature analysis and upon which broken lines have been superimposed on the waveform to depict a signature window.

After performing normalization, the controller calculates the signature coefficient SIG in block 112. Signature analysis is a new template matching method. It was created in an attempt to increase the sensitivity of template matching techniques in the context of ventricular tachycardia detection while requiring only low computational complexity. Signature analysis consists of defining, for each template waveform sample, a minimum and maximum amplitude value. These minimum and maximum values define the template window boundaries. FIG. 6 illustrates an example of a template derived from a sample intracardiac electrogram signal waveform indicating a normal sinus rhythm cardiac behavior. In this example, the controller samples only a predetermined number of samples preceding and following either the occurrence of a "SENSE" signal generated by the digital comparator 46 of FIG. 1. The sampling interval $\tau$ is delineated by respective solid lines 89 and 91 preceding and following each detected R-wave 90. The controller constructs a signature window for each sample within the sampling interval $\tau$. A normal sampling interval $\tau$ may have a duration of 80 milliseconds. If the sampling interval of the delta modulator and bandpass filter 42 of FIG. 1 is 4 milliseconds, the template and cardiac signal include 20 sample points. Dashed lines have been superimposed on the waveform of FIG. 6 to depict a signature window. The window height is set individually for each template sample. In the preferred embodiment of the invention, the maximum 93 and minimum 95 window boundaries are centered around the template R-wave 90 sample value and are set at plus and minus the maximum of either one-half the amplitude of the template sample or one-half of a predetermined minimum window value. The predetermined minimum window value is set to a value of about 20% of the initial template peak. A common minimum window value is ten.

Amplitude windowing of the signal provides the capability to account for physiological variability in the cardiac signal. If the amplitude of a signal sample lies within the window, it is considered to be a normal physiological signal. Other prior art morphology analysis methods consider any signal which is not identical to the predetermined signal to be abnormal to some degree. This is contrary to the physiological variability of the heart.

The controller counts the number of signal samples falling outside the window boundaries. The greater the number of samples outside the window, the lesser the morphologic match between the template and the signal. The result of signature analysis is a coefficient called SIG which the controller calculates according to equation 5:

$$SIG = \frac{(T_{cnt} - S_{out})}{T_{cnt}}, \qquad (5)$$

where $T_{cnt}$ is the number of template samples (or counts) having an absolute amplitude greater than one-half the predetermined minimum window value. The controller determines and stores $T_{cnt}$ in conjunction with template selection and updating in blocks 104, 106, 120, 142 and 144 (FIG. 5). The $T_{cnt}$ disregards template samples that are close to the 0 (or baseline) level which contain little of the information that distinguishes signals of different classes of cardiac activity. $S_{out}$ is the number of signal samples which fall outside the template window. The SIG coefficient has a value of 1 when all signal samples are within the template boundary. SIG values less than 0 may occur since $S_{out}$ can have a maximum value of the total number of samples in the template, while $T_{cnt}$ is usually less than the total number of template samples. The controller creates the template window during the select-sinus-rhythm.-template block 104 and adjusts the template window via update-template block 120, determine-and-store-template-counts block 142 and determine-and-store-template-window block 144.

By simply counting the number of samples falling outside the template amplitude window, the method and apparatus of the present invention prevent overemphasis of the influence of large amplitude noise spikes on cardiac signal analysis. In other prior art morphology analysis procedures, a large amplitude noise spike influences cardiac signal analysis beyond its reasonable physiological importance. The method of the present invention is independent of the amplitude of noise spikes once the amplitude is greater than the maximum template window.

In compare-SIG-to-arrhythmia-threshold block 113, the controller compares the calculated signature coefficient to a preset threshold level which defines a signature value at which the signal does not match a normal sinus rhythm waveform. For example, signature values consistent with normal sinus rhythm and sinus tachycardia waveforms may range from about 0.6 to 1.0. In the preferred embodiment of the invention, the arrhythmia threshold may include an analysis of the rate at which the heart is beating. For example, the compare-SIG-to-arrhythmia-threshold block 113 may include analysis of the SIG coefficient when the heart is beating within one or more rate windows. At heart rates below a preset minimum (e.g. 100 beats per minute (bpm)) and above a preset maximum (e.g. 200 bpm), the controller may disable the arrhythmia detection procedure of FIG. 5 since arrhythmias do not occur below the lower limit and ventricular tachycardia or ventricular fibrillation are definitely occurring at rates above the upper limit. At a heart rate above a highest level, a SIG coefficient below about 0.6 may indicate the occurrence of an arrhythmia condition. At a lower heart rate, but a rate which may be indicative of the possibility of an arrhythmia condition, a SIG coefficient below approximately 0.5 may be considered to evidence an arrhythmia condition.

In the preferred embodiment of the invention, the controller compares the number of sample points falling outside the template amplitude window to a preset maximum. The preset maximum is equal to the product of the number of template samples larger than a predetermined value and one minus the SIG arrhythmia threshold (e.g. $1-0.6=0.4$). If the number of sample points outside the template window is greater than the preset maximum, the controller initiates the control response in block 115.

If analysis of the SIG coefficient or, in some embodiments of the invention, analysis of the SIG coefficient in combination with heart rate, show evidence of the occurrence of an arrhythmia condition, the controller may initiate a control response in block 115. The respond logic block 114 controls whether the controller executes initiate-control-response block 115.

In initiate-control-response block 115, the controller may begin an arrhythmia control response such as cardioversion or one of the various known antitachycardia pacing procedures. U.S. Pat. No. 4,406,287 issued to T. A. Nappholz et al. on Sep. 27, 1983, entitled "Variable Length Scanning Burst Tachycardia Control Pacer", and U.S. Pat. No. 4,408,606 issued to R. A. J. Spurrell on Oct. 11, 1983, entitled "Rate Related Tachycardia Control Pacer", are illustrative of some of the methods of antitachycardia pacing which may be initiated by block 115.

In block 116, the controller analyzes a predetermined criterion to determine whether to update the template. This criterion includes an analysis of the SIG parameter. In the preferred embodiment of the invention, template updating takes place when SIG is greater than 0.75, the heart rate is less than a preset maximum (e.g. 150 bpm) and at least a predetermined number of cardiac cycles (for example, 100) have occurred since the previous template updating operation. More or less frequent updating is possible to accommodate more or less rapidly changing physiological signals and to conserve power. Under the control of update logic block 118, the controller updates the template in update-template block 120 if the predetermined criterion is achieved, otherwise the controller samples data for the next cardiac cycle in block 108.

In update-template block 120, the controller performs template updating to provide minor adaptation to changes in electrogram morphology which can occur over time. The controller updates each template point according to the rules of equations 6 through 8:

$$\text{If } s_i > t_i + 1, \text{ then } t_i + 1 \rightarrow t_i, \qquad (6)$$

$$\text{If } s_i < t_i - 1, \text{ then } t_i - 1 \rightarrow t_i, \qquad (7)$$

$$\text{Otherwise, } t_i \rightarrow t_i, \qquad (8)$$

where $s_i$ are the most recently acquired signal samples and $t_i$ are the template samples This template updating procedure provides gradual tracking of changes in the signal morphology. After template updating, the controller again samples data for the next cardiac cycle in block 108. Although the preferred embodiment of the invention performs template updating according to the description of equations 6, 7 and 8, alternative methods of template updating may be used in other embodiments of the invention. In one such alternative template updating method, a group of memory locations is provided for accumulating aligned sample sequences over time. These aligned sample sequences are averaged point-by-point to produce an averaged waveform template sequence.

After determining a new template sequence, the controller then analyzes the template data by counting the number of template samples having an absolute amplitude greater than the aforementioned predetermined number (for example, 5) to set and store the number of template counts $T_{cnt}$ in determine-and-store-template-counts block 142.

In determine-and-store-template-window block 144, the controller derives the template window by setting the maximum and minimum template window boundaries in a manner such as those disclosed previously.

Figure 7:
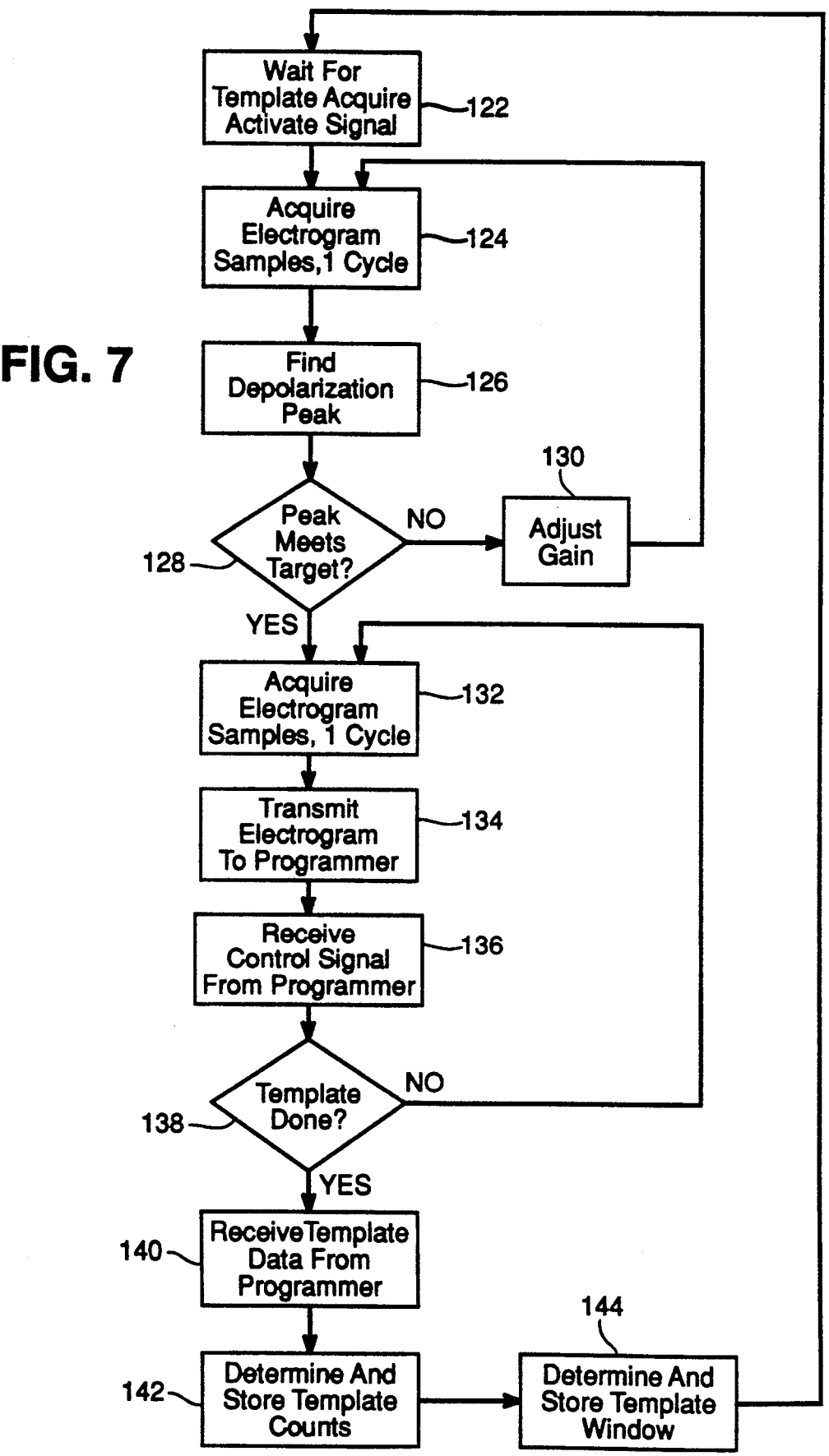
FIG. 7 is a block diagram flow chart of a template acquisition and storage procedure employed in the present invention.

A block diagram flow chart of a template acquisition and storage procedure which is performed by the controller 50 of FIG. 1 is shown in FIG. 7. In the preferred embodiment of the invention, a signal from an external programming device (not shown) activates template acquisition. Wait-for-template-acquire-activate-signal block 122 waits for the instruction code from the programmer which starts template acquisition. When the controller receives the template acquisition code, acquire-electrogram-samples,-1-cycle block 124 begins sampling electrogram data for the purpose of determining an appropriate gain setting for the electrogram signal. The controller performs an automatic gain control procedure in a loop of subprocedures comprising blocks 124 through 130 of FIG. 7. Each pass through this loop corresponds to one cardiac cycle. In acquire-electrogram-samples block 124, the controller reads a stream or sequence of incoming signal data from the delta modulator and bandpass filter block 42 of FIG. 1. The controller may input and store every sample for the duration of a cardiac cycle or may input only a predetermined number of samples preceding and following the occurrence of either the detection of a waveform peak or the "SENSE" signal which is generated by the digital comparator 46 of FIG. 1. In find-depolarization-peak block 126, the controller determines the maximum signal amplitude for the cardiac cycle and compares this amplitude to a predetermined peak value. Under the control of logic block 128, if the peak signal amplitude does not meet the target criterion, adjust-gain block 130 increases the gain setting if the signal is too low to meet the desired criterion or decreases the gain setting if the signal is too large. In the preferred embodiment of the invention, the automatic gain control procedure of blocks 124 through 130 adjusts the signal amplitude control by means of control lines CTRL from the controller 50 to the preamplifier and attenuator 40 (both of FIG. 1) on successive "SENSE" detect signals until the depolarization peak signal is approximately 80% of the entire positive or negative signal range. This may be done by waiting for the preamplifier gain setting to cross the value (determined by the 80%-of-range threshold value) five times.

When the automatic gain control procedure is complete, the controller acquires electrogram samples for subsequent cardiac cycles in block 132 and transmits this electrogram data to the programmer (not shown) in block 134. The controller may send every electrogram sample to the programmer or send only those samples which occur within a time window which begins a predetermined number of samples before a "SENSE" signal and lasts for a preset number of samples after the "SENSE" signal Alternatively, the controller may send a predetermined number of samples previous to and following the peak amplitude signal. The controller may then receive a control signal from the programmer in block 136. The control signal may inform the controller to terminate the acquisition of signal data. When the controller receives a signal to terminate template acquisition, logic block 138 directs the controller to begin receiving the template from the programmer in block 140. If the programmer does not send the signal to terminate template acquisition, the controller continues to acquire electrogram signals and send these signals to the programmer in a loop comprising blocks 132–138.

While the controller is sending the signal data in the loop of blocks 132 through 138, the programmer reads this data and derives an appropriate template data sequence. The programmer may derive the template sequence in any appropriate manner. For example, the programmer may average a number of suitable waveforms to define the template. In an interactive manner, an operator handling the programmer may select an appropriate sinus rhythm template data sequence or sequences (if waveforms are averaged). If a particular template waveform is not suitable, the operator can restart the template selection process. The template waveform should encompass the QRS complex of an electrogram. Furthermore, the template waveform should be produced from the analysis of the QRS complex of an electrogram which is characteristic of electrograms acquired when the heart is functioning in a known condition. In the preferred embodiment of the invention, the template begins 12 ms prior to the "SENSE" detect signal and has a duration of 80 ms.

When the operator has chosen an appropriate template data sequence, the programmer sends the template samples to the controller using the telemetry block 52 of FIG. 1. The controller receives this data in block 140. The controller then analyzes the template data to set the number of template counts $T_{cnt}$ in determine-and-store-template-counts block 142.

Again, in determine-and-store-template-window block 144, the controller sets the template window by setting the window to extend the delta value less than and greater than the template sample value. As was described in the discussion of FIG. 5, delta is set to the larger of either half the template sample value or half the predetermined minimum window value.

After performing block 144, the controller again waits for the programmer to issue another template acquire activation signal in block 122.

It will be apparent from the foregoing description that the present invention provides a method and apparatus for performing signature analysis on acquired cardiac signals, which method and apparatus are capable of differentiating ventricular tachycardia from sinus rhythm in a patient while accepting normal physiological signal variability, and which require only low computational complexity.

Although this invention has been described with reference to particular embodiments, it is to be understood that such embodiments are merely illustrative of the application of the principles of the invention. Numerous modifications may be made therein and other arrangements may be devised without departing from the true spirit and scope of the invention, as set forth in the appended claims.

We claim:

1. A method of detecting cardiac arrhythmias in a patient's heart, comprising the steps of:

sampling a cardiac electrical signal when the heart is functioning in a known cardiac state;

defining, for each sample of the known state cardiac electrical signal occurring within a predetermined time of interest, an amplitude window of signal amplitudes bracketing the amplitude of the known state cardiac electrical signal sample;

storing a template sequence of amplitude window samples encompassing the predetermined time of interest;

monitoring a time sequence of cardiac electrical signal samples when the heart is functioning in an unknown cardiac state;

time aligning samples of the unknown cardiac state sequence with respect to samples of the template sequence of amplitude window samples;

comparing, sample by sample, the samples of the unknown cardiac state sequence to the template sequence of amplitude window samples to determine the relative proportion of unknown cardiac state samples with amplitudes falling outside the amplitude window in comparison to unknown cardiac state samples with amplitudes falling inside the amplitude window; and classifying the functioning of the patient's heart as other than the known cardiac state when the determined relative proportion meets a predetermined criteria and, otherwise, classifying the functioning of the patient's heart as the known cardiac state.

2. A method according to claim 1, further comprising the step of normalizing the amplitudes of the unknown cardiac state sequence samples so that the average unknown cardiac state sequence sample amplitude lies within a range determined by the template sequence of amplitude window samples.

3. A method according to claim 2, wherein said time aligning step comprises the sub-steps of:

defining an alignment pointer for equating in time a sample in the unknown cardiac state sequence with a sample in the template sequence of amplitude window samples;

deriving a manifestation of the sample by sample differences between the unknown cardiac state and the template sequence of amplitude window samples;

shifting said alignment pointer with respect to one sequence of the unknown cardiac state and the template sequences of amplitude window samples;

repeating said deriving and shifting sub-steps until said deriving step has been performed with respect to multiple alignment pointers; and comparing each of said derived manifestations to determine the alignment pointer associated with the best match between the unknown cardiac state sequence and the template sequence of amplitude window samples.

4. A method according to claim 3, wherein said manifestation of the sample by sample differences is derived by summing, over the length of the sequences, the absolute values of the differences between each of the template sequence of amplitude window samples and its alignment pointer-corresponding unknown cardiac state sequence sample.

5. A method according to claim 3, wherein said manifestation of the sample by sample differences is derived by comparing, sample by sample, the samples of the unknown cardiac state sequence with the template sequence of amplitude window samples to determine the relative proportion of unknown cardiac state samples having amplitudes falling outside the amplitude window in comparison to unknown cardiac state samples having amplitudes falling inside the amplitude window.

6. A method according to claim 1, wherein said time aligning step comprises the sub-steps of:

defining an alignment pointer for equating in time a sample in the unknown cardiac state sequence with a sample in the template sequence of amplitude window samples;

deriving a manifestation of the sample by sample differences between the unknown cardiac state and the template sequence of amplitude window samples;

shifting said alignment pointer with respect to one sequence of the unknown cardiac state and the template sequence of amplitude window samples;

repeating said deriving and shifting sub-steps until said deriving step has been performed with respect to multiple alignment pointers; and comparing each of said derived manifestations to determine the alignment pointer associated with the best match between the unknown cardiac state sequence and the template sequence of amplitude window samples.

7. A method according to claim 6, wherein said manifestation of the sample by sample differences is derived by summing, over the length of the sequences, the absolute values of the differences between each of the template sequence of amplitude window samples and its alignment pointer-corresponding unknown cardiac state sequence sample.

8. A method according to claim 6, wherein said manifestation of the sample by sample differences is derived by cardiac state sequence with the template sequence of amplitude window samples to determine the relative proportion of unknown cardiac state samples having amplitudes falling outside the amplitude window in comparison to unknown cardiac state samples having amplitudes falling inside the amplitude window.

9. A method of detecting cardiac arrhythmias in a patient's heart, comprising the steps of:

sensing cardiac electrical signals when the heart is functioning in a known cardiac state;

characterizing cardiac electrical signal samples occurring within a predetermined time of interest when the heart is functioning in said known cardiac state;

storing said known cardiac state samples as a time sequence of template samples;

defining an array of amplitude ranges bracketing said timing sequence of template samples;

storing said array of amplitude ranges in a time sequence of window ranges corresponding sample by sample to said time sequence of template samples;

subsequently monitoring a time sequence of cardiac electrical signal samples when the heart is functioning in an unknown cardiac state;

reconstructing a template sequence of amplitude window samples from said stored time sequence of template samples and said time sequence of window amplitude ranges;

time aligning samples of said unknown cardiac state sequence with respect to said reconstructed template sequence of amplitude window samples;

comparing time aligned samples of said unknown cardiac state sequence with said reconstructed template sequence of amplitude window samples;

ascertaining the number of the compared time aligned samples of said unknown cardiac state sequence having amplitudes outside of said reconstructed template sequence of amplitude window samples;

comparing said ascertained number of unknown cardiac state sequence samples having amplitudes outside said template sequence of amplitude window samples with a threshold value; and classifying said unknown cardiac state sequence within said known cardiac state when the ascertained number of monitored samples having amplitudes outside said template sequence of amplitude window samples is less than said threshold value, and classifying said unknown cardiac state as other than said known cardiac state when the ascertained number of monitored samples having amplitudes outside said template sequence of amplitude window samples is greater than said threshold value.

10. A method according to claim 9, further comprising the step of normalizing the amplitudes of the unknown cardiac state sequence samples, wherein said normalizing step comprises the sub-steps of:

summing the absolute values of the amplitudes of the time sequence of template samples;

subsequently summing the absolute values of the amplitudes of the unknown cardiac state sequence samples;

determining the difference between said template sequence sum and said unknown cardiac sequence sum;

ascertaining a normalization factor from this difference value for multiplying the unknown cardiac state sequence sum to place this sum within a predetermined range of said template sequence sum; and multiplying each sample of the unknown cardiac state sequence by said normalization factor.

11. A method according to claim 10, wherein said time aligning step comprises the sub-steps of:

defining an alignment pointer for equating in time a sample in the unknown cardiac state sequence with a sample in the time sequence of template samples;

deriving a manifestation of the sample by sample differences between the unknown cardiac state sequence and the time sequence of template samples;

shifting said alignment pointer with respect to one sequence of the unknown cardiac state sequence and the time sequence of template samples;

repeating said deriving and shifting sub-steps until said deriving step has been performed with respect to multiple alignment pointers; and comparing each of said derived manifestations to determine the alignment pointer associated with the best match between the unknown cardiac state sequence and the time sequence of template samples.

12. A method according to claim 11, wherein said manifestation of the sample by sample differences is derived by summing, over the length of the sequences, the absolute values of the differences between each of the time sequence of template samples and its alignment pointer-corresponding unknown cardiac state sequence sample.

13. A method according to claim 9, wherein said time aligning step comprises the sub-steps of:

defining an alignment pointer for equating in time a sample in the unknown cardiac state sequence with a sample in the time sequence of template samples;

deriving a manifestation of the sample by sample differences between the unknown cardiac state sequence and the time sequence of template samples;

shifting said alignment pointer with respect to one sequence of the unknown cardiac state sequence and the time sequence of template samples;

repeating said deriving and shifting sub-steps until said deriving step has been performed with respect to multiple alignment pointers; and comparing each of said derived manifestations to determine the alignment pointer associated with the best match between the unknown cardiac state sequence and the time sequence of template samples.

14. A method according to claim 13, wherein said manifestation of the sample by sample differences is derived by summing, over the length of the sequences, the absolute values of the differences between each of the time sequence of template samples and its alignment pointer-corresponding unknown cardiac state sequence sample.

15. A method according to claim 13, wherein said manifestation of the sample by sample differences is derived by comparing, sample by sample, the samples of the unknown cardiac state sequence with the template sequence of amplitude window samples to determine the relative proportion of unknown cardiac state samples having amplitudes falling outside the amplitude window in comparison to unknown cardiac state samples having amplitudes falling inside the amplitude window.

16. A cardiac arrhythmia detector for detecting cardiac arrhythmias in a patient's heart, comprising:

means for sampling a cardiac electrical signal when the heart is functioning in a known cardiac state;

means for defining, for each sample of the known state cardiac electrical signal occurring within a predetermined time of interest, an amplitude window of signal amplitudes bracketing the amplitude of the known state cardiac electrical signal sample;

means for storing a template sequence of amplitude window samples encompassing the predetermined time of interest;

means for monitoring a time sequence of cardiac electrical signal samples when the heart is functioning in an unknown cardiac state;

means for time aligning samples of the unknown cardiac state sequence with respect to samples of the template sequence of amplitude window samples;

means for comparing, sample by sample, the samples of the unknown cardiac state sequence to the template sequence of amplitude window samples to determine the relative proportion of unknown cardiac state samples with amplitudes falling outside the amplitude window in comparison to unknown cardiac state samples with amplitudes falling inside the amplitude window; and means for classifying the functioning of the patient's heart as other than the known cardiac state when the determined relative proportion meets a predetermined criteria and, otherwise, classifying the functioning of the patient's heart as the known cardiac state.

17. A detector according to claim 16, further comprising a means for normalizing the amplitudes of the unknown cardiac state sequence samples so that the average unknown cardiac state sequence sample amplitude lies within a range determined by the template sequence of amplitude window samples.

18. A detector according to claim 16, wherein said time aligning means further comprises:
 means for defining an alignment pointer for equating in time a sample in the unknown cardiac state sequence with a sample in the template sequence of amplitude window samples;
 means for deriving a manifestation of the sample by sample differences between the unknown cardiac state and the template sequence of amplitude window samples;
 means for shifting said alignment pointer with respect to one sequence of the unknown cardiac state and the window window sequence of amplitude window samples;
 means for repeating the operations of said deriving and shifting means until said deriving means has acted with respect to multiple alignment pointers; and
 means for comparing each of said derived manifestations to determine the alignment pointer associated with the best match between the unknown cardiac state sequence and the template sequence of amplitude window samples.

19. A detector according to claim 18, wherein said deriving means further comprises:
 means for subtracting unknown cardiac state sequence samples from time aligned samples of said template sequence of amplitude window samples on a sample by sample basis;
 means for determining the absolute values of each difference sample determined by said subtracting means; and
 means for summing said absolute values over the length of the sequences.

20. A detector according to claim 18, wherein said time aligning means further comprises:
 means for defining an alignment pointer for equating in time a sample in the unknown cardiac state sequence with a sample in the template sequence of amplitude window samples;
 means for deriving a manifestation of the sample by sample differences between the unknown cardiac state and the template sequence of amplitude window samples;
 means for shifting said alignment pointer with respect to one sequence of the unknown cardiac state and the template sequence of amplitude window samples;
 means for repeating the operations of said deriving and shifting means until said deriving means has acted with respect to multiple alignment pointers; and
 means for comparing each of said derived manifestations to determine the alignment pointer associated with the best match between the unknown cardiac state sequence and the template sequence of amplitude window samples.

21. A detector according to claim 20, wherein said deriving means further comprises:
 means for subtracting unknown cardiac state sequence samples from time aligned samples of said template sequence of amplitude window samples on a sample by sample basis;
 means for determining the absolute values of each difference sample determined by said subtracting means; and
 means for summing said absolute values over the length of the sequences.

22. A cardiac arrhythmia detector for detecting cardiac arrhythmias in a patient's heart, comprising:
 means for sensing cardiac electrical signals when the heart is functioning in a known cardiac state;
 means for characterizing cardiac electrical signal samples occurring within a predetermined time of interest when the heart is functioning in said known cardiac state;
 means for storing said known cardiac state samples as a time sequence of template samples;
 means for defining an array of amplitude ranges bracketing said time sequence of template samples;
 means for storing said array of amplitude ranges in a time sequence of window ranges corresponding sample by sample to said time sequence of template samples;
 means for subsequently monitoring a time sequence of cardiac electrical signal samples when the heart is functioning in an unknown cardiac state;
 means for reconstructing a template sequence of amplitude window samples from said stored time sequence of template samples and said time sequence of window amplitude ranges;
 means for time aligning samples of said unknown cardiac state sequence with respect to said reconstructed template sequence of amplitude window samples;
 means for comparing time aligned samples of said unknown cardiac state sequence with said reconstructed template sequence of amplitude window samples;
 means for ascertaining the number of the compared time aligned samples of said unknown cardiac state sequence having amplitudes outside of said reconstructed template sequence of amplitude window samples;
 means for comparing said ascertained number of unknown cardiac state sequence samples having amplitudes outside said template sequence of amplitude window samples with a threshold value; and
 means for classifying said unknown cardiac state sequence within said known cardiac state when the ascertained number of monitored samples having amplitudes outside said template sequence of amplitude window samples is less than said threshold value, and classifying said unknown cardiac state as other than said known cardiac state when the ascertained number of monitored samples having amplitudes outside said template sequence of amplitude window samples is greater than said threshold value.

23. A detector according to claim 22, further comprising a means for normalizing the amplitudes of the unknown cardiac state sequence samples, wherein said normalizing means further comprises:

means for summing the absolute values of the amplitudes of the time sequence of template samples;

means for subsequently summing the absolute values of the amplitudes of the unknown cardiac state sequence samples;

means for determining the difference between said template sequence sum and said unknown cardiac sequence sum;

means for ascertaining a normalization factor from this difference value for multiplying the unknown cardiac state sequence sum to place this sum within a predetermined range of said template sequence sum; and means for multiplying each sample of the unknown cardiac state sequence by said normalization factor.

24. A detector according to claim 22, wherein said time aligning means further comprises:

means for defining an alignment pointer for equating in time a sample in the unknown cardiac state sequence with a sample in the time sequence of template samples;

means for deriving a manifestation of the sample by sample differences between the unknown cardiac state and the time sequence of template samples;

means for shifting said alignment pointer with respect to one sequence of the unknown cardiac state and the time sequence of template samples;

means for repeating the operations of said deriving and shifting means until said deriving means has acted with respect to multiple alignment pointers; and means for comparing each of said derived manifestations to determine the alignment pointer associated with the best match between the unknown cardiac state sequence and the time sequence of template samples.

25. A detector according to claim 24, wherein said deriving means further comprises:

means for subtracting unknown cardiac state sequence samples from time aligned samples of said time sequence of template samples on a sample by sample basis;

means for determining the absolute values of each difference sample determined by said subtracting means;

means for summing said absolute values over the length of the sequences.

26. A detector according to claim 24, wherein said time aligning means further comprises:

means for defining an alignment pointer for equating in time a sample in the unknown cardiac state sequence with a sample in the time sequence of template samples;

means for deriving a manifestation of the sample by sample differences between the unknown cardiac state and the time sequence of template samples;

means for shifting said alignment pointer with respect to one sequence of the unknown cardiac state and the time sequence of template samples;

means for repeating the operations of said deriving and shifting means until said deriving means has acted with respect to multiple alignment pointers; and means for comparing each of said derived manifestations to determine the alignment pointer associated with the best match between the unknown cardiac state sequence and the time sequence of template samples.

27. A detector according to claim 26, wherein said deriving means further comprises:

means for subtracting unknown cardiac state sequence samples from time aligned samples of said time sequence of template samples on a sample by sample basis;

means for determining the absolute values of each difference sample determined by said subtracting means; and means for summing said absolute values over the length of the sequences.

28. A detector according to claim 26, wherein said deriving means further comprises:

means for comparing, sample by sample, the samples of the unknown cardiac state sequence with the template sequence of amplitude window samples to determine the relative proportion of unknown cardiac state samples having amplitudes falling outside the amplitude window in comparison to unknown cardiac state samples having amplitudes falling inside the amplitude window.

29. A method of detecting cardiac arrhythmias in a patient's heart, comprising the steps of:

selecting samples of the patient's physiologically normal cardiac electrical signal;

defining for each of the selected samples an amplitude window delineating a range of signal amplitudes bracketing the amplitude of the normal cardiac electrical signal sample;

subsequently monitoring the patient's cardiac electrical signal when the heart is operating in an unknown cardiac state by sampling said cardiac electrical signals, comparing said samples to time-corresponding defined amplitude windows and counting the relative number of samples wherein the sample amplitude falls outside the amplitude window; and classifying said unknown cardiac state as either a normal state or an arrhythmia state as a function of said relative number of samples.

30. A cardiac arrhythmia detector for detecting cardiac arrhythmias in a patient's heart, comprising:

a sensor for sensing, amplifying and digitizing cardiac electrical signals, said cardiac electrical signals being indicative of a normal physiological state at certain times and being indicative of an arrhythmia cardiac state at other times, and a controller, said controller further comprising:

means for selecting samples of the patient's physiologically normal cardiac electrical signal;

means for defining for each of the selected samples an amplitude window delineating a range of signal amplitudes bracketing the amplitude of the normal cardiac electrical signal sample;

means for subsequently monitoring the patient's cardiac electrical signal when the heart is operating in an unknown cardiac state by sampling said cardiac electrical signals and by calculating a signature function by comparing said samples to time-corresponding defined amplitude windows and counting the relative number of samples wherein the sample amplitude falls outside the amplitude window; and means for classifying said unknown cardiac state as either a normal state or an arrhythmia state as a function of said signature function.

* * * * *